(12) United States Patent
Marin et al.

(10) Patent No.: US 12,369,790 B2
(45) Date of Patent: Jul. 29, 2025

(54) METHOD AND INSTRUMENT FOR PROVIDING AT LEAST ONE EYE OF A SUBJECT WITH A FIRST REFRACTION CORRECTION AND WITH A SECOND REFRACTION CORRECTION TO BE COMPARED WITH EACH OTHER

(71) Applicant: Essilor International, Charenton-le-Pont (FR)

(72) Inventors: Gildas Marin, Charenton-le-Pont (FR); Adéle Longo, Charenton-le-Pont (FR); Guillaume Giraudet, Charenton-le-Pont (FR); Stéphane Boutinon, Charenton-le-Pont (FR); Philippe Pinault, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 828 days.

(21) Appl. No.: 17/615,760

(22) PCT Filed: Jun. 4, 2020

(86) PCT No.: PCT/EP2020/065429
§ 371 (c)(1),
(2) Date: Dec. 1, 2021

(87) PCT Pub. No.: WO2020/245247
PCT Pub. Date: Dec. 10, 2020

(65) Prior Publication Data
US 2022/0304569 A1 Sep. 29, 2022

(30) Foreign Application Priority Data
Jun. 6, 2019 (EP) .................................. 19305733

(51) Int. Cl.
*A61B 3/028* (2006.01)
*A61B 3/00* (2006.01)
*A61B 3/103* (2006.01)

(52) U.S. Cl.
CPC .......... *A61B 3/0285* (2013.01); *A61B 3/0008* (2013.01); *A61B 3/0025* (2013.01); *A61B 3/028* (2013.01); *A61B 3/103* (2013.01)

(58) Field of Classification Search
CPC ..... A61B 3/0008; A61B 3/0025; A61B 3/028; A61B 3/0285; A61B 3/103
See application file for complete search history.

(56) References Cited

U.S. PATENT DOCUMENTS 4,105,303 A  8/1978 Guyton
5,148,205 A  9/1992 Guilino et al.
(Continued)

FOREIGN PATENT DOCUMENTS

CN  103429140 A  12/2013
CN  108542346 A  9/2018
(Continued)

OTHER PUBLICATIONS

Japanese Office Action issued Oct. 23, 2023 in Japanese Patent Application No. 2021-572034 (with English Translation), 6 pages.
(Continued)

*Primary Examiner* — Jack Dinh
(74) *Attorney, Agent, or Firm* — Oblon, McClelland, Maier & Neustadt, L.L.P.

(57) ABSTRACT

A method and associated instrument in which an optical system is switched from a first to a second refractive power states, to provide a first, and then a second refraction correction to an eye of a subject, the switching being carried on without interrupting a light beam coming from a target object and transmitted by the optical system to the eye of the (Continued)

subject. The switching is carried on in order to circumvent an intermediate refraction correction that is in between said first and second refraction corrections, or with a speed higher than a given limit.

14 Claims, 3 Drawing Sheets

(56) References Cited

U.S. PATENT DOCUMENTS

| | | |
|---|---|---|
| 2006/0007397 A1 | 1/2006 | Lai |
| 2015/0042951 A1 | 2/2015 | Stanga et al. |
| 2015/0355480 A1 | 12/2015 | Contet et al. |
| 2016/0331226 A1 | 11/2016 | Nauche et al. |
| 2017/0108711 A1 | 4/2017 | Muschielok et al. |
| 2017/0108712 A1 | 4/2017 | Guilloux |

FOREIGN PATENT DOCUMENTS

| | | |
|---|---|---|
| CN | 108885355 A | 11/2018 |
| EP | 2 835 097 A1 | 2/2015 |
| JP | 2017-509024 A | 3/2017 |
| WO | WO 2014/128035 A1 | 8/2014 |
| WO | WO 2015/173381 A1 | 11/2015 |
| WO | WO 2018/202713 A1 | 11/2018 |

OTHER PUBLICATIONS

International Search Report and Written Opinion issued on Sep. 21, 2020 in PCT/EP2020/065429 filed Jun. 4, 2020, 13 pages.

Thibos, L., et al., "Accuracy and precision of objective refraction from wavefront aberrations", Journal of Vision, vol. 4, 2004, pp. 329-351.

Office Action issued Apr. 14, 2025 in Chinese Patent Application No. 202080041030.0, in English, citing documents 1, 2 and 15-17 therein.

METHOD AND INSTRUMENT FOR PROVIDING AT LEAST ONE EYE OF A SUBJECT WITH A FIRST REFRACTION CORRECTION AND WITH A SECOND REFRACTION CORRECTION TO BE COMPARED WITH EACH OTHER

TECHNICAL FIELD OF THE INVENTION

The invention relates to a method for providing a subject with a first refraction correction and with a second refraction correction, to be compared with each other by the subject.

The invention concerns also an optometry instrument configured to implement such a method.

BACKGROUND INFORMATION AND PRIOR ART

During a subjective refractometry protocol, to determine a refraction feature of an eye of the subject, such as a spherical power of a refractive error of this eye, different refraction corrections are generally provided to the eye of the subject. The subject then indicates which one of these refraction corrections enables him to best see a target object, with a minimum amount of blur.

To get gradually closer to an optimal refraction correction, that best compensates for the refractive error of the eye of the subject, it is usual to provide successively to the eye of the subject a first refraction correction, and then a second refraction correction that is close to the first one. The subject is then asked to indicate which one of these two corrections enables him to have the best vision of the target object.

Depending on the result of the comparison of these two corrections, an average refractive power of this set of first and second refraction corrections may be increased, or decreased, until the subject indicates that these two corrections lead to similar, and low amounts of blur. In this situation, for which the first and second corrections lead to similar amounts of blur, the average refractive power mentioned above is close to the one that best compensates for the refractive error of the eye of the subject.

In some optometric instruments, to switch from the first refraction correction to the second refraction correction, a given set of lenses, initially placed in front of the eye of the user, is replaced by another set of lenses. During this lenses substitution, the target object is temporarily masked to the subject. Cutting off the field of view of the eye of the subject in this way prevents the subject from being able to compare finely the first and second refraction corrections. In other words, because of this cut off, the subject is able to compare the first and second refraction corrections, that is to indicate which one is the best, only if they are sufficiently different from each other, as his perception is, to some extent, reset as a result of said cut off.

Other optometric instruments have an optical system, through which the subject looks at the target object, that enables to modify the refraction correction provided to the eye of the user without cutting off his field of view. Such an optical system may be realized by means of a continuously deformable lens having an adjustable refractive power, as described in document WO 2017/013343, for instance. Such an optometric instrument should enable the subject to compare said corrections even when they are close to each other, thus leading to an estimation of the refractive feature of the eye having a better precision.

However, even with such an optometric instrument, in which the refraction correction is continuously varied with no cut off, it turns out in practice that the comparison between said first and second refraction corrections remains difficult for the subject and is not well repeatable when these refraction corrections are close to each other, particularly in the vicinity of the optimal refraction correction.

SUMMARY OF THE INVENTION

Therefore one object of the disclosure is to provide a method for providing at least one eye of a subject with a first refraction correction and with a second refraction correction to be compared with each other, in which switching from the first refraction correction to the second refraction correction is carried on without cutting off the field of view of the eye of the subject, and which enable the subject to finely compare these first and second refraction corrections even if they are close to each other. This is achieved by an appropriate control of the blur variations, during the switching from the first to the second refraction corrections.

This method, in which an optical system transmits a light beam coming from a target object to the eye of the subject, comprises a step of switching the optical system from:
a first refractive power state, in which the optical system provides said first refraction correction to the eye of the subject, to
a second refractive power state, in which the optical system provides said second refraction correction to the eye of the subject, said switching being carried on without interrupting the light beam transmitted by the optical system,
each refractive power state of the optical system being represented by a corresponding point, in a coordinate system, the coordinates of said point being representatives of the values, for said refractive power state of the optical system, of different refractive power features of the optical system,
the first refractive power state being represented by a first point and the second refractive power state being represented by a second point in said coordinate system, a line segment starting at said first point and ending at said second point, an optimal refraction correction for the eye of the subject being represented by an optimal refraction point in said coordinate system.

Remarkably, in this method:
when an intermediate point, located on a medial part of said line segment is closer to the optimal refraction point or farther from the optimal refraction point than each of said first and second points,
then, said switching is carried on so that:
for each point of a trajectory representing said switching, a distance in said coordinate system between said point and the intermediate point is higher than or equal to one fourth of the smallest of: a first distance between said first point and said intermediate point, and a second distance between said second point and said intermediate point, or so that
a speed of variation of a refractive power of said optical system, at the point of said trajectory that is the closest to said intermediate point, is higher than a speed of variation limit above which the subject is unable to perceive a refractive power change.

One explanation for the difficulty to compare the first and second refraction corrections, in the case of a progressive or even continuous switching between them, is that, during said switching, when in the vicinity of the optimal refraction correction of said eye, an intermediate refraction correction provided to the eye of the subject during said switching, which corresponds to said intermediate point, often correspond to a blur level, perceived by the subject, that is markedly lower than the blur levels corresponding to first and second refraction corrections to be compared.

It turns out that perceiving such a reduced blur level, in the course of switching from said first and second refraction corrections, makes the comparison of the first and second refraction corrections more difficult for the subject.

Similarly, when said intermediate point is farther from the optimal correction point than said first and second points (that is to say, when the distance, in said coordinate system, between the intermediate point and the optimal refraction point is higher than the distance between the first point and the optimal refraction point, and higher than the distance between the second point and the optimal refraction point), passing through the intermediate point during said switching causes a significant blur level increase. In other words, in this case, the blur level perceived by the subject when the optical system is, statically, in its intermediate refraction state, is higher than the blur levels corresponding to the first and second refraction states. It turns out also to disturb the subject and to make the comparison of the first and second refraction corrections more difficult for the subject.

Switching the optical system from its first to its second refractive power states while remaining distant from the intermediate point, or at a speed higher than said speed of variation limit (at least during a part of said switching), prevents the subject from perceiving the blur level corresponding to said intermediate refraction correction, which, in the cases mentioned above, is substantially different (lower or higher) from the blur levels corresponding to the first and second refraction corrections.

This feature thus enables to reduce unnecessary and potentially disturbing blur variations, during said switching, compared to a switching performed at low or moderate speed and along a rectilinear trajectory, in said coordinate system (and that would thus pass, slowly, by said intermediate point). And it turns out that reducing these blur variations improves the accuracy and repeatability of the comparison of these first and second refraction corrections by the subject.

Optional, non-limiting features of the method for providing said first and second refraction corrections are defined, according to the invention, by claims 2 to 14.

Besides, the method may also comprise the following steps, executed before providing said first and second refraction corrections to the eye of the subject:
  acquiring personal data relative to the subject; and
  determining coordinates of the first and second points that represent said first and second refractive power states, on the basis of said personal data.

The above mentioned object is also achieved according to the invention by providing an instrument. The optional features of the method mentioned above can also be applied to this device.

DETAILED DESCRIPTION OF EXAMPLE(S)

The following description with reference to the accompanying drawings will make it clear what the invention consists of and how it can be achieved. The invention is not limited to the embodiment/s illustrated in the drawings. Accordingly, it should be understood that where features mentioned in the claims are followed by reference signs, such signs are included solely for the purpose of enhancing the intelligibility of the claims and are in no way limiting on the scope of the claims.

Figure 1:
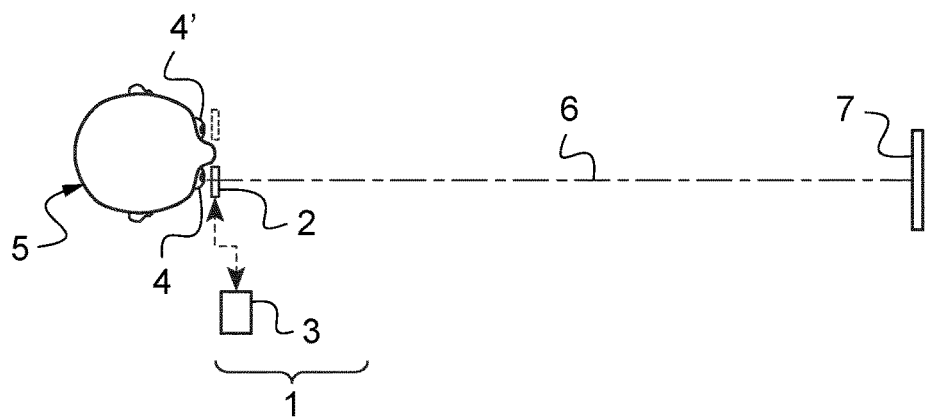
FIG. 1 represents schematically, from above, some elements of an instrument for providing an eye of a subject with refraction corrections to be tested by the subject.

Instrument for Providing an Eye of a Subject with Refraction Corrections to be Tested by the Subject FIG. 1 represents schematically a subject 5, looking at a target object 7 through an optical system 2 that provides his/her eye 4 with an adjustable refraction correction, in order to test the subject's vision and to determine at least one refraction feature of his/her eye 4.

This optical system 2 is part of an instrument 1, which comprises also a control unit 3 for controlling the optical system 2 in order to modify the refraction correction provided to the subject during an eye exam. The instrument may comprise another optical system (not represented on the figures), similar the one mentioned above, for the determination of a refraction error of the other eye 4' of the subject.

The target object 7 may be a screen or a panel, displaying one or several optotypes, or any image appropriate to test the vision of the subject.

The optical system 2 is configured to provide the eye 4 of the subject with an adjustable cylindrical refraction correction, in order to determine astigmatism features of this eye. So, the optical system 2 is configured so that its cylindrical refractive power features, like its "cylinder" and the axis of this "cylinder", can be adjusted.

In the embodiments described here, the optical system 2 is further configured to provide this eye 4 with an adjustable spherical refraction correction. In other words, the spherical refractive power of the optical system 2 is also adjustable.

The optical system 2 is configured so that its refractive power features, mentioned above, can be adjusted gradually, by small steps or even continuously.

The optical system 2 is configured also so that its refractive power features can be modified without interrupting the light beam 6 that comes from the target object 7 and that passes through the optical system 2 to reach the eye 4 of the subject. This light beam 6 is constituted by the part of the light that comes from the target object 7 and that is collected by the optical system 2 and then transmitted to the eye 4 of the subject 5 (this light being initially emitted, diffused or reflected by the target object). The optical system 2 is thus configured so that its refractive power features can be modified with no cut-off of the field of view of the eye 4 of the subject. In other words, the target object 7 remains unmasked, that is to say unclogged, to the eye 4 of the subject in the course of such a refractive power modification. In particular, the optical system 2 is configured so that such a refractive power features adjustment can be achieved without substituting a given lens by another (which would temporarily mask the target object to the eye of the subject).

The optical system 2 comprises one or more lenses and/or mirrors. At least one of these lenses and/or mirrors:
- is movable, having a position relative to the target object that can be controlled by the control unit 3 of the instrument 1, or
- has an adjustable shape, that can be controlled by the control unit 3.

So, the configuration of the optical system 2 can be modified in a controlled manner, by the control unit 3, in order to modify at least some of the refractive power features of the optical system 2.

The optical system 2 may comprise, for instance, a single, deformable liquid lens having said adjustable shape, such as disclosed in EP3096677. It may also comprise such a deformable lens and additional optical components, and/or a deformable mirror, an Alvarez lens, or a light field display. It may also comprise a Badal-like system comprising at least one lens and a displacement system to modify a length of an optical path joining the target object to this lens, in order to form an image of the target object 7 at a distance from the eye 4 of the subject that is adjustable.

In the embodiments described here, the optical system 2 forms an image of the target object 7 at a distance from the eye of the subject 4 that is adjustable, which enables to test if this eye is narrow or far-sighted, or else. The spherical refractive power of the optical system 2, that is the spherical refraction correction provided to this eye 4 by the optical system 2 (which, in the case of a Badal-like system, is a kind of effective spherical refractive power), is directly related to the distance at which the optical system 2 forms the image of the target object 7. The spherical refractive power of the optical system 2 can be defined as being equal, or approximately equal, to the inverse of the algebraic distance between the eye 4 of the subject and the image of the target object 7 formed by the optical system 2.

More generally, the optical system 2 is optically equivalent to a single lens, that would be placed in front of the eye 4 of the subject, close to the eye 4 (not further than a three centimeters) and that would provide this eye 4 with an image of an object that is located at a fixed, long distance ahead of the subject (at several meters, or even infinitely far), this effective lens having adjustable refractive power features. The cylindrical refractive power features of the optical system 2 are the cylindrical refractive power features of this equivalent lens. The same applies to the spherical refractive power of the optical system. For example, in the particular case in which the optical system 2 comprises the single, deformable, liquid lens mentioned above, and in which the target object 7 is located several meters away from the subject, the equivalent lens mentioned above is this single liquid lens itself.

The expression "refractive power state" of the optical system 2 refers to an ensemble of refractive power features the optical system 2 has when it is in a given configuration, providing the eye 4 of the subject with a given refraction correction. Each refractive power state of the optical system 2 may be defined, as it is the case here, by the ensemble of values of at least three different refractive power features of the optical system 2, the optical system being in this given configuration. One of these three refractive power features is related to, or even representative of the spherical refractive power of the optical system 2. The others two refractive power features mentioned above are representative of a first cylindrical refractive power feature of the optical system 2 and a second, distinct cylindrical refractive power feature of the optical system 2.

Each refractive power state of the optical system 2 can thus be represented by a corresponding point, in a coordinate system. The coordinates of this point are representative of the values, for said refractive power state of the optical system, of the three different refractive power features mentioned above.

These three coordinate can be, for instance:
- the spherical refractive power of the optical system 2, also named the sphere S of the optical system;
- the cylinder C of the optical system 2;
- an angle $\alpha$ representative of the orientation of an axis of the cylinder of the optical system 2.

The sphere S can be defined as the refractive power (sometimes named optical power), of the equivalent lens mentioned above, that is given by the spherical component of the shape of the front and back faces of this equivalent lens.

The cylinder C can be defined as the refractive power, of this equivalent lens, that is given by the cylinder component of the shape of the front and back faces of this equivalent lens.

The angle $\alpha$ is formed between a fixed, reference direction and the axis on which is centered the cylinder component mentioned above.

Another vector decomposition of the cylinder components of the optical system 2 could be used to characterize the cylindrical refractive power features of the optical system 2, instead of the magnitude and orientation decomposition mentioned above (that is to say instead of specifying the cylinder, and orientation of the cylinder).

For example, the refractive power state of the optical system 2 could be represented by the three orthogonal components (M, J0, J45), instead of the three spherocylindrical components (Sphere S, Cylinder C, orientation a), where J0 and J45 are the refractive powers of two Jackson crossed cylinders lenses representative of the cylindrical refractive power features of the optical system 2 and where M is the spherical equivalent, equal to the sphere S, plus half of the cylinder C: M=S+C/2. The cylinders of the first of these two "Jackson lenses" are orientated at 45 degrees from the cylinders of the other of these "Jackson lenses". When the first "Jackson lens" is aligned with the reference direction mentioned above, that is to say when one of its crossed cylinders is aligned with this direction, the first crossed cylinders power J0 is equal to $(-C/2)*\cos(2*\alpha)$, while the second crossed cylinders power J45 is equal to $(-C/2)*\sin(2*\alpha)$.

Another coordinate system that could be employed to represent the refractive power state of the optical system 2 is based on a Zernike polynomials decomposition of a characteristic wavefront, outputted by the optical system 2 when it is illuminated by a point source, instead of the target object 7, this point source being located at the same position than the target object 7. The three components mentioned above are then the three second-order coefficients $c^o_2$, $c^2_2$ and $c^{-2}_2$ of this Zernike polynomials decomposition. It is noted that this coordinate system is equivalent to the one based on the three orthogonal components M, J0 and J45, as the three second-order coefficients $c^o_2$, $c^2_2$ and $c^{-2}_2$ are proportional to M, J0 and J45 respectively, according to formula 1 of the article of Thibos et al. cited further below.

Other coordinate systems than those described above could be employed, to represent the refractive power states of the optical system 2.

Figure 6:
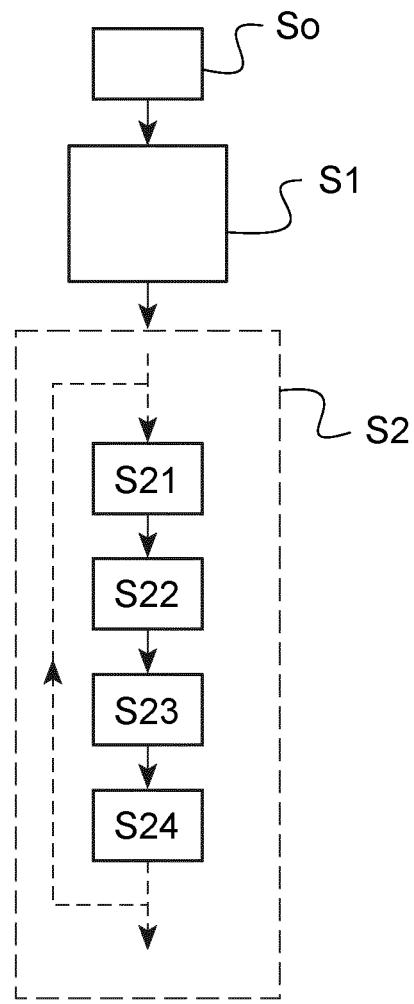
FIG. 6 represents schematically some steps of a subjective refraction protocol.

The control unit 3 is programmed to control the optical system 2 in order to provide the eye 4 of the subject with various refraction corrections, according to a refraction protocol, for instance according to the refraction protocol of FIG. 6, in order to determine refraction errors of the eye 4 of the subject.

In particular, the control unit 3 is programmed in order to implement the method, for providing the eye 4 of the subject with a first and a second refraction corrections to be compared with each other, that is described below. According to this method, the optical system 2 switches from:
- a first refractive power state, in which the optical system 2 provides this first refraction correction to the eye 4 of the subject, to
- a second refractive power state, in which the optical system 2 provides this second refraction correction to the eye 4 of the subject.

The subject 5 then specifies which one of these first and second corrections enables him/her to best see the target object 7 (sharper, darker, and/or less distorted vision of the target object), for instance by inputting this information by means of a user interface of the instrument 1.

Such a comparison step plays an important role in several refraction protocols. It enables for instance to get gradually closer to an optimal refraction correction that best compensates for the refractive errors of the eye 4 of the subject, as explained further below with reference to FIG. 6.

The first and second refractive power states, between which the optical system switches, are represented respectively by a first point P1 and by a second point P2, in the coordinate system mentioned above (FIGS. 2 to 4).

In prior art instruments, when such a switching is carried on, continuously, with no cut off of the subject's field of view, the trajectory representing the switching is usually rectilinear, constituted of a line segment [P1P2] starting at the first point P1 and ending at the second point P2.

But when the first and second corrections are in the vicinity of the optimal refraction correction of the eye 4 of the subject, an intermediate point $P_I$, located on a medial part of this line segment, for instance in the middle of this line segment, is most often closer to an optimal refraction point $P_O$, that represents the optimal refraction correction, than the first point P1 and the second point P2. In other words, in such a situation, the intermediate refraction correction, represented by the intermediate point $P_I$, corrects the refraction errors of the subject better than the first refraction correction and than the second refraction correction. So, with the prior art instrument mentioned above, switching from the first to the second refraction corrections causes a blur level perceived by the subject to decrease temporarily, during the switching. Indeed, the blur level corresponding to the intermediate refraction correction is both lower than the one corresponding to the first refraction correction, and lower than the one corresponding to the second refraction correction. This is disturbing for the subject 5 and prevents him from a reliable, repeatable comparison of the first and second refraction corrections. The expression "optimal refraction correction" refers to a refraction correction, that would be determined, in conclusion to a subjective refraction protocol, as correcting optimally the refraction errors of the eye 4 of subject.

Conversely, in situations somehow opposite to the optimal refraction correction, switching from the first to the second refraction corrections while following a rectilinear path may cause the blur level perceived by the subject to temporary increase during the switching (instead of temporary decrease), which is also disturbing for the subject.

In the method according to the invention, to avoid these undesirable effects, the control unit 3 of the instrument 1 controls the optical system 2 so that,
when an intermediate point $P_I$, located on the medial part of the line segment mentioned above, is closer to the optimal refraction point $P_O$ than each of said first and second points P1 and P2, or, alternatively, farther from the optimal refraction point $P_O$ than each of said first and second points P1 and P2,
then, during said switching:
i) for each point P of a trajectory representing said switching in said coordinate system, a distance d between said point P and the intermediate point $P_I$ in said coordinate system is higher than or equal to one fourth of the smallest of: a first distance d1 between said first point P1 and said intermediate point $P_I$, and a second distance d2 between said a second point P2 and said intermediate point $P_I$, or
ii) a speed of variation $s_V$ of the refractive power of the optical system 2, at the point of said trajectory that is the closest to said intermediate point $P_I$, is higher than a speed of variation limit $s_L$, above which the subject 5 is unable to perceive a refractive power change.

Switching the optical system 2 from its first to its second refractive power states while remaining distant from the intermediate point $P_I$, or at a speed higher than said speed of variation limit $s_L$ during at least a part of said switching, prevents the subject 5 from perceiving the blur level corresponding to said intermediate refraction correction, which, in the cases mentioned above, is substantially different (lower or higher) from the blur levels corresponding to the first and second refraction corrections.

This feature thus enables to reduce unnecessary and potentially disturbing blur variations, during said switching, which improves the accuracy and repeatability of the comparison of these first and second refraction corrections by the subject 5.

As an alternative, or as a complement the control unit 3 may control the optical system 2 so that the switching is carried on according to feature i) or ii) when a distance, between the intermediate point $P_I$ and the optimal refraction point $P_O$ or between the intermediate point $P_I$ and an estimate of optimal refraction point, is smaller than one fourth, or alternatively one half of the smallest of the first distance and the second distance.

In the embodiments described here, the distances between points, in said coordinate system, are each equal to the Euclidian distance between the points considered, that is to say equal to the "ordinary" straight-line distance. Though, in other embodiments, the distances between points in said coordinate system could be determined according to other metrics, for instance as being equal to the sum of the respective absolute values of:
- the difference between the first coordinate of the first point and the first coordinate of the second point considered;
- the difference between the second coordinate of this first point and the second coordinate of this second point; and
- the difference between the third coordinate of this first point and the third coordinate of this second point, this kind of distance being sometimes referred to as the "city block distance", or "Manhattan distance".

The particular way to switch from the first to the second refractive power states of the optical system 2, that has been presented above, is described in detail below in the section "switching from the first to the second refraction correction", and illustrated by six different switchings, corresponding to a same set of first and second refractive power states. Then, the subjective refraction protocol represented in FIG. 6, based on the method for providing the eye 4 of the subject with the first and second refraction corrections mentioned above, is described from a more general point of view in the section "subjective refraction protocol".

Switching from the First Refraction to the Second Refraction Correction

In practice, the distance d12 between the first and second points P1 and P2, that represent these two corrections in the coordinate system, typically ranges from 0.1 to 2 diopters.

This distance d12 can be set to a constant value, independently of the subject. It may also be set depending on a sensitivity of the subject regarding refraction variations. This sensitivity may be characterized by the value of a sensitivity parameter, such as the one described in the European patent application no 18305996.3 own by the applicant (and not yet published, at the date of filing of the present patent application). This sensitivity parameter is representative of, for instance equal to, the smallest variation, of one or several optical features of a lens placed in front of the eye 4 of the subject, that may be perceived by the subject 5. The distance d12 mentioned above may be all the smaller as this sensitivity parameter is small.

It is further noted, that, in the embodiments described here, the control unit 3 is programmed in order to make the optical system 2 to switch from the first to the second refractive power states in accordance with feature i) or ii) above when the middle of the line segment [P1P2] is closer to, or alternatively farther from, the optimal refraction point $P_O$ than each of the first and second points P1 and P2. In this case the intermediate point $P_I$, that is circumvented by the trajectory representing the switching, or in the vicinity of which this trajectory passes quickly, is the middle of this line segment.

Figure 2:
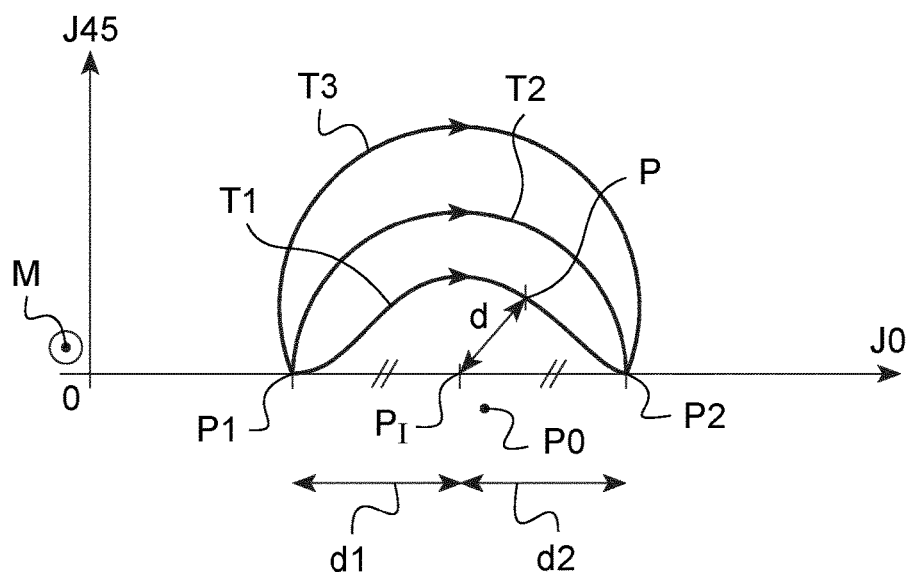
FIGS. 2, 3 and 4 represent schematically different trajectories for switching an optical system of the instrument of FIG. 1 from a first refractive power state to a second refractive power state.
Figure 3:
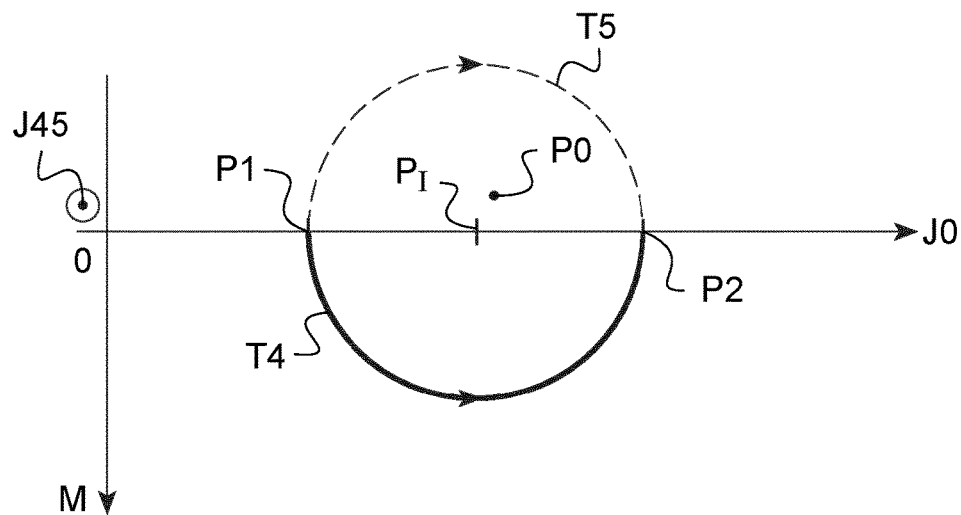
Figure 4:
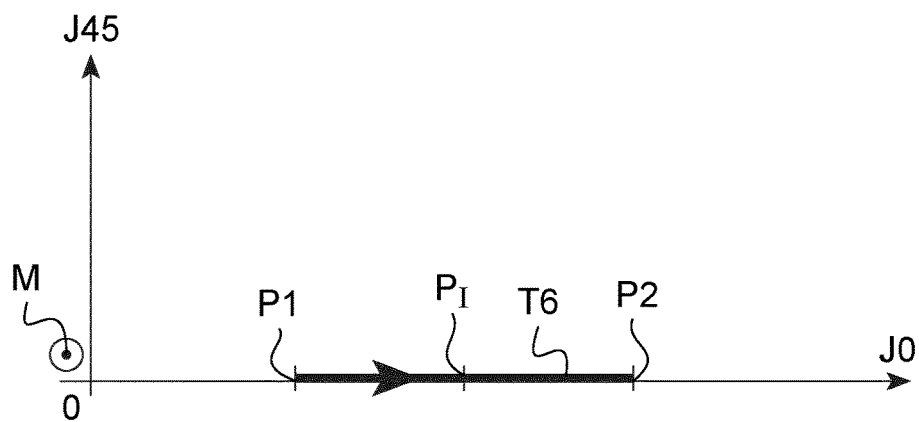

This situation corresponds, inter alia, to the case represented in FIGS. 2 to 4, for which the middle of the line segment [P1P2] is closer to the optimal refraction point $P_O$ than each of the first and second points P1 and P2 (that is to say that the distance, in said coordinate system, between the middle of the line segment and the optimal refraction point $P_O$ is smaller than the distance between the first point P1 and the optimal refraction point $P_O$, and smaller than the distance between the second point P2 and the optimal refraction point $P_O$).

As the intermediate point $P_I$ is then located at the middle of the line segment [P1P2], the first distance d1 (distance between points P1 and $P_I$) is equal to the second distance d2, and the base distance $d_m$, that is "the smallest of the first and second distances d1, d2", is equal indifferently to d1 or d2: $d_m=d1=d2$.

It is noted however, that, in other situations, the middle of the line segment [P1P2] may not be closer to, or farther from the optimal refraction point $P_O$ than each of the first and second points P1 and P2, while an other point of the medial part of this line segment would be closer to, or farther from the optimal refraction point $P_O$ than each of the first and second points P1 and P2. In such a case, the intermediate point, that would be circumvented by the trajectory representing the switching, or in the vicinity of which this trajectory would pass quickly, would be this other point.

Besides, the control unit 3 could be further programmed to control the optical system 2 so that:
when the intermediate point $P_I$ is closer to the optimal refraction point $P_O$ than each of said first and second points P1 and P2, or, alternatively, farther from the optimal refraction point $P_O$ than each of said first and second points P1 and P2,
then, during said switching, for each point P of the trajectory representing said switching, the distance d between said point P and the intermediate point $P_I$ is higher than an approach distance threshold $d_{ap}$, this approach distance threshold $d_{ap}$ being higher to 0.05 diopter, or even higher to 0.125 diopter.

The control unit 3 could also be programmed to control the optical system 2 so that
when the intermediate point $P_I$ is closer to the optimal refraction point $P_O$ than each of said first and second points P1 and P2, or, alternatively, farther from the optimal refraction point $P_O$ than each of said first and second points P1 and P2, then, during said switching:
i') for each point P of the trajectory representing said switching, a distance between said point P and each point of the medial part of the line segment [P1P2] is higher than or equal to one fourth of the base distance $d_m$ (as it is the case for the trajectories T2 to T5 described below), or
ii') the speed of variation $s_V$ of the refractive power of the optical system 2 is higher than the speed of variation limit $s_L$ mentioned above for each point of said trajectory that is located at a distance of the intermediate point $P_I$ that is smaller than one fourth, or even one half, of the base distance $d_m$ (as it is the case for the switching corresponding to trajectory T6).

So, according to this last feature, it is not only the intermediate point $P_I$ that is circumvented, or in the vicinity of which the system passes quickly, but the whole medial part of the line segment [P1P2].

The medial part of the line segment [P1P2] (which, itself, is a—smaller—line segment), has a length equal to one half of the length of this line segment. The middle of this medial part coincides with the middle of the line segment. Alternatively, the length of the medial part of the line segment could be smaller, for instance equal to one fourth of the length of the line segment [P1P2].

The six trajectories T1 to T6 represented in FIGS. 2 to 4 illustrate more specifically different switchings of the optical system 2 that could be achieved by the instrument 1, according to the invention.

The three coordinates, of the coordinate system in which these trajectories are represented, are the spherical equivalent M of the optical system 2, and the first and second crossed cylinders power J0 and J45. Though, as mentioned above, other coordinate systems could be employed to represent the refractive power states of the optical system 2.

The first point P1, from which each of these trajectories T1, T2, T3, T4, T5, T6 begins, and the second point P2, at which it ends, are the same for these six trajectories. Whether in the first refractive power state represented by the first point P1, or in the second refractive power state represented by the second point P2, the optical system 2 has the same spherical equivalent power M (in other words, the same total spherical power), for these six switchings. Indeed, here, the comparison of the first and second refraction corrections by the subject is carried on in order to determine the astigmatism features of his/her eye 4.

In the particular situation represented on these figures, the first and second points P1 and P2 correspond both to values of the spherical equivalent M that are substantially equal to zero, and to values of the coordinate J45 are also substantially equal to zero. The value of the spherical equivalent M is slightly negative for the optimal correction point P0, which is otherwise close to middle of the line segment [P1P2].

Of course, the switching technique described here applies also to other sets of first and second refractive power states. For example, instead of corresponding to the same orientation of the axis of the cylinder of the optical system 2 and to different values of this cylinder (as in the case represented on the figures), the two refractive power states to be compared by the subject may correspond to the same value of cylinder C of the optical system 2, but to two different orientations of this cylinder (to two different values of the angle α).

The first five trajectories, T1 to T5, are trajectories that remain distant from the intermediate point $P_I$ (FIGS. 2 and 3).

For each point P of the first trajectory T1 (FIG. 2), the distance d between this point and the intermediate point $P_I$ is comprised between one half of the base distance $d_m$, and this base distance: $d_m/2 \le d \le d_m$. As a variant, the distance d could be comprised between one fourth of the base distance $d_m$, and this base distance.

For any of the second, fourth and fifth trajectories, T2, T4 and T5, for each point of the trajectory considered, the distance d between this point and the intermediate point $P_I$ is equal to the base distance $d_m$: $d=d_m$. So, each of these trajectories, T2, T4 and T5, is a half circle centered on the intermediate point $P_I$ (FIGS. 2 and 3). Such half circle trajectories permit to minimize the temporary blur level variations occurring during the switching, leading to a very comfortable and reliable comparison of the first and second refractive power states. More generally, this advantageous effect could be obtained for trajectories such that the distance d remains comprised between 0.8 times the base distance $d_m$, and 1.2 times the base distance $d_m$.

And the third trajectory T3 is such that, for each point of this trajectory, the distance d between this point and the intermediate point $P_I$ is higher than or equal to the base distance $d_m$: $d \ge d_m$. More particularly, except for the first and second points P1, P2, the distance d is higher than $d_m$: $d > d_m$.

All along the first trajectory T1, the spherical equivalent M of the optical system 2 remains constant. The same applies to the second and third trajectories T2 and T3. So, in the coordinate system considered here, these trajectories are planar.

The fourth and fifth trajectories T4 and T5 are also planar, but, along them, the spherical equivalent M of the optical system 2 varies, while one of the cylindrical refractive power features of the optical system 2 (as represented, J45) remains constant.

The fourth trajectory T4 circumvents the intermediate point $P_I$ by increasing, and then decreasing the spherical equivalent M, while one of the cylindrical refractive power features of the optical system 2 (as represented, J0) is varied to reach the second point P2.

So, all along this trajectory, the spherical equivalent M of optical system 2 varies while remaining higher than the smallest of: a first value of the spherical equivalent M, M1, corresponding to the first point P1, and a second value of spherical equivalent M, M2, corresponding to the second point P2. This feature prevents advantageously the eye 4 of the subject from accommodating. In other words, thanks to this feature, all along said switching, the eye 4 of the subject focuses on a point located as far as possible from this eye.

The fifth trajectory T5 is similar to the fourth one, but circumvents the intermediate point PI by decreasing, and then increasing the spherical equivalent M, while the cylindrical refractive power features mentioned above (J0) is varied to reach the second point P2. The fifth trajectory is represented by a dashed line while the fourth trajectory is represented by an unbroken line, in FIG. 4.

Other trajectories circumventing the intermediate point $P_I$, different from trajectories T1 to T5, could be followed to switch from the first to the second refractive power states, in particular non-planar trajectories.

Besides, instead of avoiding the intermediate point $P_I$, the trajectory representing the switching from the first to the second refraction correction could pass through this point, like the sixth trajectory T6, but at high speed.

This sixth trajectory T6 is rectilinear (FIG. 4), and, thus, coincides with the line segment [P1P2].

During this sixth switching, the speed of variation $s_V$ of the refractive power of the optical system, at the intermediate point $P_I$ (that is to say when said trajectory passes through said intermediate point), is higher than the speed of variation limit $s_L$.

More specifically, during this switching, the speed of variation $s_V$ is all the higher as the distance d, between the intermediate point $P_I$ and the point P that represents the refractive power state of the optical system 2, is small.

The speed of variation $s_V$ of the refractive power of the optical system 2 is the speed at which the point P, that represents the current refractive power state of the optical system 2, moves on the trajectory representing the switching, in the coordinate system. It may be expressed in diopters per second, for instance.

So, for example, when the value of the cylinder C of the optical system 2 remains constant while its orientation varies, the speed of variation is equal to $C \cdot (d\alpha/dt)$ (with α expressed in radians).

Figure 5:
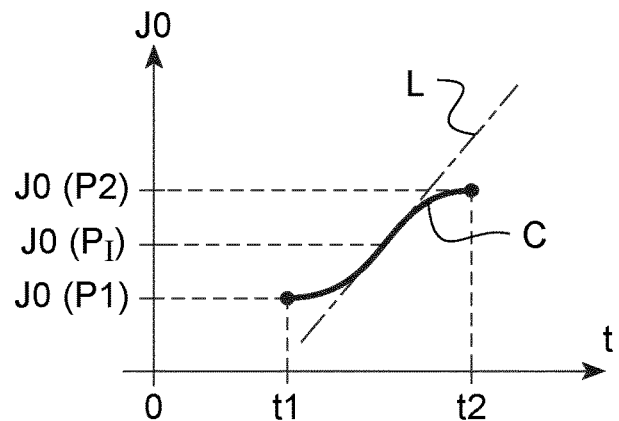
FIG. 5 represents schematically the evolution over time of a cylindrical power feature of the optical system, for the switching corresponding to FIG. 4.

And in the particular case represented in FIG. 4, as the spherical equivalent M and the coordinate J45 remain constant during the switching, the speed of variation $s_V$ is equal to $d(J0)/dt$. So, in this case, at the intermediate point $P_I$ for instance, the slope of the line L, that is tangent to the curve $\mathscr{C}$ representing the variation of the coordinate J0 over time t, is higher than the speed of variation limit $s_L$. This curve is represented in FIG. 5.

The speed of variation limit $s_L$ is the highest speed of variation of refractive power for which the subject 5 is able to perceive a refractive power variation.

In other words, when the refractive power of the refraction correction provided to the eye of the subject varies over time with a speed higher than the speed of variation limit $s_L$, the subject is unable to perceive this variation.

And when the refractive power of the refraction correction provided to the eye of the subject varies over time with a speed lower than the speed of variation limit $s_L$, the subject is able to perceive, at least partially, this variation.

To determine the speed of variation limit $s_L$ of a subject, a skilled vision scientist, optometrist can submit to a subject an image to be seen through the optical system 2 set at a first refractive power, and change the refractive power to a second refractive power with an initial speed variation $s_I$. The subject has only 2 alternative forced choices: 2 options of response: YES, I do see a change; NO, I don't. If the subject says YES, the first and second refractive powers are maintained the same but the speed of variation is increased. When the subject answers NO, the speed is decreased. Using classical psychophysical staircase methods, the speed variation limit $s_L$ can be defined as such for each individual.

For almost any subject, when the speed of variation of the refractive power is higher than 20 diopters per second, it turns out that the subject cannot perceive the corresponding refractive power variation. So, in practice, 20 diopters per second is a suitable value of the speed of variation limit $s_L$. Indeed, when the switching from the first to the second refractive power states is carried on with a speed higher than this value, even if the trajectory followed by the optical system 2 passes through the intermediate point $P_I$, the subject 5 cannot perceive the corresponding reduced blur level, or, alternatively, the increased blur level corresponding to the intermediate point.

10 diopters per second is also a suitable value of the speed of variation limit $s_L$, as this value is still high enough that most subjects cannot perceive the reduced/increased blur level corresponding to the intermediate point $P_I$, when the trajectory passes through this point with such a speed.

Figure 7:
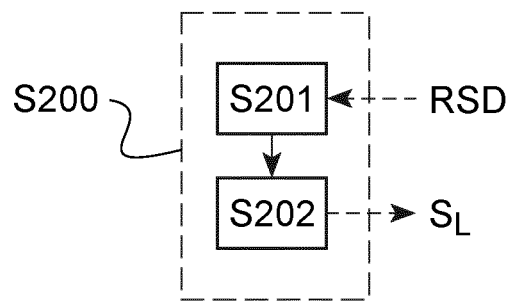
FIG. 7 represents schematically some steps for determining a speed of variation limit of a refractive power of said optical system.

In the embodiments of the method described here, the speed of variation limit $s_L$ is determined, during a step S200, before switching from the first to the second refractive power state (FIG. 7). This step may be executed by the control unit 3 of the optical instrument 1. The step S200 comprises the following steps:
  acquiring data relative to a response speed, with which the subject 5 reacts to a refractive power change (step S201); and
  determining the speed of variation limit $s_L$ on the basis of said data (step S202).

The data relative to the subject's response speed, referred to as RSD, may comprise:
  the age of the subject 5; the ocular state/properties such as the transparency of the intraocular environment, the presence of a pathology, visual performances: high and low contrast visual acuity, type and level of ametropia, data relative to the installation of the subject: such as the vertex distance that can impact the magnification of the system, therefore the apparent size of the stimulus, and thus potentially the RSD, data relative to the stimuli: the type of the target and the distance to which it is put relative to the subject . . .
  a previous value of response speed, determined during other tests realized prior to said method, this previous value being, for instance, loaded from a remote server or read into an electronic health card of the subject 5;
  a set of response times, with which the subject 5 had reacted during tests previously carried on in the course of the same refraction protocol (for instance in the course of the refraction protocol of FIG. 6).

In step S202, when the data relative to the subject's response speed, RSD, comprises the previous value of response speed mentioned above, then, the value of the speed of variation limit $s_L$ may be set to be equal to this previous value.

When this data comprises the above mentioned set of response times, the speed of variation limit $s_L$ may be determined so as to be all the higher as these response times are short.

And when this data comprises the age of the subject, the speed of variation limit $s_L$ may then be determined as explained below, depending on a nominal maximum speed of variation $s_{max}$ of the optical system 2 and on the age of the subject.

The nominal maximum speed of variation $s_{max}$ of the optical system 2 is the highest speed of variation of the optical power of the optical system 2 for which the optical system 2 is designed. In other words, it is the highest speed of variation that the optical system 2 can achieve repeatedly and without damaging the optical system or excessive heating. The nominal maximum speed of variation $s_{max}$ may for instance be comprised between 15 and 50 diopters per second, depending on the optical system 2 considered.

The speed of variation limit $s_L$ is then determined so as to be equal to a portion of this nominal maximum speed of variation $s_{max}$, this portion being all the higher as the subject is young.

For instance, when the age of the subject is smaller than 20 years, then the speed of variation limit $s_L$ may be set to the nominal maximum speed of variation $s_{max}$, and preferably higher than 20 diopters per second.

When the age of the subject is comprised between 20 and 50 years, then, the speed of variation limit $s_L$ may be set to 70 percent (70%) of the nominal maximum speed of variation $s_{max}$, and preferably higher than 10 diopters per second.

And when the age of the subject is above 50 years, then, the speed of variation limit $s_L$ may be set to 50 percent (50%) of the nominal maximum speed of variation $s_{max}$, and preferably higher than 5 diopters per second.

As the speed of variation limit $s_L$ is adapted to the age of the subject, the optical power of the optical system 2 is varied at its nominal maximum speed of variation $s_{max}$ only when necessary (only if the subject is young), thus preventing unnecessary heating or wear of the optical system.

The value of the speed of variation limit $s_L$ may also be determined, in step S202, by combining the value determined on the basis of the age of the subject, the previous value of response speed, and/or the value deduced from the set of response times mentioned above. This combination may be achieved, for instance, by averaging these three values.

The value of the speed of variation limit $s_L$ may also take into account the sensitivity parameter of the subject. In particular, the value of the speed of variation limit $s_L$ may be set all the higher as the minimal refraction variation that can be detected by the subject is small. Indeed, when the subject is very sensitive to refraction variations, it is preferable to set the speed of variation limit $s_L$ to a high value as the subject would otherwise notice clearly the temporary blur level variation caused by the proximity of the optimal refraction point $P_O$ (as the subject is very sensitive to the value of the refraction provided to him/her). In case of failure of step S201 (for instance because the data relative to the subject's response speed RSD are not available), or if the control unit 3 determines that these data are not sufficient/sufficiently reliable, the speed of variation limit $s_L$ may be set, in step S202, to a default value, for instance equal to 20, to 10 diopters per second, or to the nominal maximum speed of variation $s_{max}$ of the optical system 2.

Alternatively, step S200 could comprise the speed of reaction test mentioned above, instead of comprising the steps of acquiring response speed data of the subject and then deducing an appropriate value of the speed of variation limit $s_L$ from this data. In other words, in the method described here, the speed of variation limit $s_L$ of the subject could be assessed directly, by performing this speed of reaction test, the above mentioned switching being then carried on depending on the speed of variation limit thus measured.

As described above, for trajectories T1 to T5, a temporary decrease of the blur level perceived by the subject 5 during the switching is avoided by remaining distant from the intermediate point $P_I$, in the coordinate system. And for the switching corresponding to the sixth trajectory T6, the trajectory passes close to, and even through, the intermediate point $P_I$, but at high speed.

The temporary blur level variation mentioned above could also be avoided, or at least reduced, by combining the geometrical and temporal features mentioned above, that is to say by remaining distant from the intermediate point $P_I$ and, at the same time, by achieving the switching at high speed, at least in the vicinity of the intermediate point. In particular, for each point P of the trajectory that is followed during the switching, the speed of variation of the refractive power $s_V$ could be all the higher as this point P is close to the intermediate point $P_I$, to avoid staying for a long time in the vicinity of the intermediate point $P_I$.

More specifically, in the method according to the invention, to avoid staying for a long time in the vicinity of the intermediate point $P_I$, the switching may be carried on so that:

an integral Int over time t, from a beginning until an end of said switching, along the trajectory representing said switching, of a given cost function $f$, the argument of which being the distance d between a current, variable point P of said trajectory and said intermediate point $P_I$, is smaller than an in-proximity time span limit $\Delta_T$ multiplied by the value of said cost function $f$ when its argument is equal to one fourth of the smallest of said first distance d1 and said second distance d2, that is to say when its argument is equal to one fourth of said base distance $d_m$.

So, according to this criterion:

$$Int = \int_{P1}^{P2} f(d[P]) \cdot dt \leq f\left(\frac{d_m}{4}\right) \cdot \Delta_T. \quad (F1)$$

The integral Int of formula F1 corresponds to a kind of average switching time, in which the time spent by the system near a given point P of the trajectory is weighted by the cost function $f(d[P])$.

The cost function $f$ is all the higher as its argument, d, is small. In other words, the cost function increases as the point P gets closer to the intermediate point $P_I$. This permits, in the integral Int, to strongly penalize the points that are close to the intermediate point PI, as the corresponding weight is high. So, during a switching for which formula F1 is fulfilled, passing close to the intermediate point at low or moderate speed is avoided, and so, the temporary variation of the blur level perceived by the subject that would otherwise occur, is avoided.

In practice, a value of the in-proximity time span limit $\Delta_T$ typically ranges from 1 millisecond to 1 second, preferably between 10 milliseconds and 0.3 second, or even, like here, between 25 and 250 milliseconds. Such values turn out to be short enough so that, for almost any subject, the transitory reduced blur level (or conversely, the transitory increased blur level) corresponding to the intermediate point $P_I$ is not perceived by the subject.

The beginning of the switching is the time t1 at which the switching starts, that it to say to the time at which the refractive power features of the optical system 2 become different from those corresponding to the first refraction correction. Similarly, the end of the switching is the time t2 at which the refractive power features of the optical system 2 become equal to those corresponding to the second refraction correction. These starting and ending times t1 and t2 are represented in FIG. 5, in the case of the sixth switching described above.

The value of the cost function $f$ may, for instance, be:

equal to zero when the distance d is above an in-proximity distance $d_p$, this in-proximity distance $d_p$ being for instance equal to half the base distance $d_m$, and positive when the distanced is below this in-proximity distance $d_p$.

Figure 8:
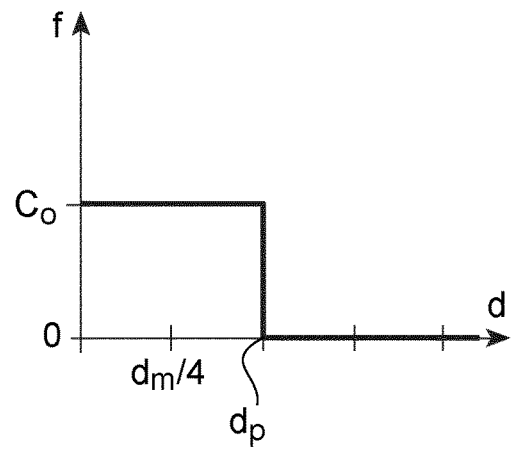
FIG. 8 is a schematic graph of a cost function that depends on a distance between two refractive corrections.

More specifically, as represented in FIG. 8, the value of the cost function $f$ may be zero when d is above $d_p$, and equal to a positive constant Co otherwise.

Other cost functions, increasing more progressively when the point P gets closer to the intermediate point $P_I$ than the one of FIG. 8, could be employed, in formula F1.

It is noted that, if we consider the cost function $f$ of FIG. 8, for example, then, for the five first trajectories T1 to T5 presented above, the criterion of formula F1 is fulfilled, as the integral Int is then equal to zero, and is thus smaller than $f(d_m/4) \cdot \Delta_T$.

And for the switching corresponding to the sixth trajectory T6, when the speed of variation of the refractive power $s_V$ is for instance constant on the part of the trajectory that corresponds to the medial part of the line segment [P1P2], equal to vo=20 diopters per second, then, one finds that the integral Int is equal to $Co \cdot d_m/vo$, which is smaller than $f(d_m/4) \cdot \Delta_T = Co \cdot \Delta_T$ as $d_m/vo$ is equal to 25 milliseconds for a typical $d_m$ of 0.5 diopter, while $\Delta_T$ is comprised between 25 and 250 milliseconds. So, for this sixth trajectory, and for such values of the various parameters, the criterion of formula F1 is also fulfilled.

It is further noted, that according to an optional feature of the method according to the invention, the switching of the optical system 2 from its first to its second refractive power state could be carried on so that, for each point P of the trajectory representing said switching, a blur level BL, that is determined on the basis of a theoretical model of the eye 4 and vision of the subject 5, and that takes into account that the eye 4 of the subject is provided with a correction corresponding to the refractive power state associated to said point P is:

higher than the product of a margin coefficient k by the minimum of a first blur level BL1 associated to the first refractive power state of the optical system and of a second blur level BL2 associated to its second refractive power state, and smaller than the ratio of the maximum of the first blur level BL1 and the second blur level BL2 by the margin coefficient k.

In other words, for each point P of the trajectory representing said switching, the corresponding blur level BL(P) then complies with formula F2 below:

$$BL(P) > k \times Min(BL1, BL2) \text{ and } BL(P) < [Max(BL1, BL2)]/k \quad (F2).$$

The margin coefficient k is comprised between 0.5 and 1, or even preferably between 0.8 and 1.

The first and second blur levels BL1 and BL2 are determined, as the blur level BL, on the basis of the theoretical model of the eye 4 and vision of the subject 5 mentioned above, and taking into account that the eye 4 of the subject is provided with the first refraction correction, or with the second refraction correction respectively.

In order to satisfy the criterion of formula F2, a trajectory, along which this last criterion is fulfilled, may be computed prior to the switching, the optical system 2 being then controlled by the control unit 3 so that it follows this pre-computed trajectory.

The blur levels determined on the basis of this model represent in a realistic and precise manner the blur levels supposed to be perceived by the subject in the beginning, in the course, and at the end of the switching.

Achieving the switching so that the above criterion is fulfilled ensures that the blur variations, perceived by the subject, are tightly limited during the switching, the blur level perceived by the subject remaining bounded approximately between the first and the second blur levels BL1 and BL2, which correspond to the beginning and end points of the switching.

The theoretical model mentioned above may assume that the eye 4 of the subject is perfectly corrected from an optical point of view, its optical resolution being then limited by diffraction only for instance, when provided with the intermediate refraction correction corresponding to the intermediate point $P_I$, or, alternatively, when provided with an other refraction correction considered as optimal for the eye of the subject. This other refraction correction may correspond to the optimal refraction point $P_O$, or to an estimate of the optimal refraction correction. So, according to this theoretical model, an optical resolution of the eye 4 such as a width of its point spread function is calculated, for each refraction correction considered, on the basis of the difference between this correction and the intermediate refraction correction, considered as a reference, perfect correction (or, alternatively, on the basis of the difference between the refraction correction to be assessed and the refraction correction considered as optimal mentioned above).

Under this assumption, the blur level BL can then be determined as a function of any of the following:
- a width of the point spread function,
- a spatial frequency cutoff of an optical modulation transfer function,
- a Strehl ratio
  of the eye 4 of the subject, provided with the refraction correction considered, and modeled as explained above.

So, when the blur level BL is determined as the width of the point spread function of this theoretical eye provided with said refraction correction, it is assumed, for example, that if the eye of the subject would be provided with the refraction correction corresponding to the intermediate point, then, this point spread function would be diffraction-limited (the eye of the subject being then supposed to be perfectly corrected).

The theoretical model of the eye 4 and vision of the subject 5 may take into account neural features of the visual response of the subject. For example, it is known that the spatial frequencies that are perceived the best by a subject are not necessarily the lowest ones. So, the blur level BL may be determined, for instance, as a spatial frequency cutoff of a visual modulation transfer function, that takes into account both optical and neural features of the eye 4 and vision of the subject, as described in the Appendix of the article "Accuracy and precision of objective refraction from wavefront aberrations", Journal of Vision (2004) 4, 329-351, by L. N. Thibos et al.

Similarly, the blur level BL could be determined as a visual Strehl ratio, that takes into account both optical and neural features of the eye 4 and vision of the subject (as described in the article mentioned above), his/her eye being provided with the refraction correction considered.

Subjective Refraction Protocol

FIG. 6 represents schematically some steps of a subjective refraction protocol, implemented by means of the instrument 1, and based on the method, described above, for providing the eye 4 of the subject with the first and second refraction corrections.

This protocol starts with a preliminary data acquisition step So, during which personal data relative to the subject 5 are acquired by the instrument 1. These personal data comprise for instance data relative to a refraction error of the eye 4 of the subject, like:
- a former refraction prescription concerning the subject 5, this prescription being, for instance, inputted by means of a user interface of the instrument 1, loaded from a remote server, read into an electronic health card of the subject 5, or determined from ophthalmic lenses usually worn by the subject 5;
- a preliminary refraction prescription, obtained by executing an objective refraction protocol prior to the subjective refraction protocol described here.

These data may comprise also the data relative to the subject's response speed, RSD, described above.

These data may comprise also data relative to the sensitivity parameter of the subject, which is representative of his/her sensitivity to refraction variations.

The protocol may also comprise the reaction speed test mentioned above, during which an individual value of the speed of variation limit $s_L$ is determined for the subject 5 whose vision is being tested.

After this data acquisition step So, the protocol comprises a spherical refraction sub-protocol, represented by step S1. During this spherical refraction sub-protocol, an optimal spherical refraction correction Mop, that best corrects the spherical refraction error of the eye 4 of the subject, is determined. To this end, the eye of the subject may be provided with refraction corrections appropriate to fog his vision (by means of spherical corrections higher than the optimal spherical refraction correction Mop), and then to progressively defog his vision until the subject indicates that he sees the target object 7 as sharply as possible. The spherical refraction obtained in this way may then be refined, or confirmed, by means of a duochrome test.

The way this spherical refraction sub-protocol is conducted may take into account at least some of the personal data acquired at step So, in order to converge to the optimal spherical refraction correction Mop quickly and/or with a precision appropriate in view of the sensitivity parameter of the subject.

The steps So and S1 are both optional. In practice, the eye care professional that supervises the protocol may choose to perform step So only, step S1 only, or both of them (and not necessarily in the order presented above).

Anyhow, prior to the step S2 described below, the optimal spherical refraction correction Mop, or at least an estimate of it, is acquired or determined.

During step S2, a cylindrical refraction sub-protocol is performed. During this cylindrical refraction sub-protocol, a cylindrical refraction correction, that best corrects the spherical refraction error of the eye 4 of the subject, is determined. To this end, the spherical refraction correction provided to the subject may be slightly increased, compared to the optimal spherical refraction correction Mop (for instance, +0.5 diopters may be added to Mop), to slightly fog the subject's vision. Then, various cylindrical refraction corrections, to be assessed, are provided to the subject.

More particularly, this cylindrical refraction sub-protocol comprises a step S23 of providing the eye 4 of the subject with the first and then the second refraction corrections to be compared with each other. The subject 5 then specifies which one of these first and second corrections enables him/her to best see the target object 7, in step S24.

Before providing the subject with the first refraction correction, and then switching to the second refraction (during step S23), the control unit 3:

determines the coordinates of these first and second refraction corrections, at step S21, and, then determines the features of the switching from this first, to this second refraction corrections, at step S22.

In the embodiment described here, the set of steps S21 to S24 is executed several times successively, until the control unit 3 determines that the optimal refraction correction of the eye 4 of the subject has been reached, or until the control unit has determined this optimal refraction correction, on the basis of the answers provided by the subject during the successive executions of step S24.

More particularly, the control unit 3 may be programmed to control the instrument 1 so that the set of steps S21 to S24 is repeated for different values of an average refraction correction, corresponding to the average of the first and second refraction corrections, until the subject indicates at step S24 that the levels of blur he perceives are identical for the first and for the second refraction corrections, and that they are low.

The optimal refraction correction may then be determined by the control unit 3 as being equal to the average refraction correction in this last situation, for which the blur levels corresponding to the first and second refractions are identical. The control unit may determine the optimal refraction correction on the basis of this last average refraction, but taking also into account previous answers provided by the subject 5 in the course of the protocol.

In this sequence of repetitions of the set of steps S21 to S24, when step S21 is executed again, the coordinates of the first and second refraction corrections (that is to say the coordinates of the first and second points P1, P2) are determined as a function of the answer or answers provided by the subject 5 during one or several previous executions of step S24.

For instance, if an answer provided by the subject during a previous execution of step S24 indicates that the first and second refraction corrections were close to the optimal refraction correction, then the control unit 3 may determine the new coordinates of the first and second refraction corrections so that these new refraction corrections are closer to the previous ones than during former repetitions of the set of steps S21 to S24. In other words, the gap between a previous first refraction correction, provided during a previous execution of step S23, and the next first refraction correction, provided during the next execution of step 23, decreases as this refraction correction gets closer to the optimal refraction correction.

The control unit 3 may determine that the first and second refraction corrections have become close to the optimal refraction correction when the answer provided by the subject at step S24 expresses a high degree of uncertainty of the subject regarding which one of the first and second refraction corrections best corrects his vision.

The control unit 3 may also determine that the first and second refraction corrections have become close to the optimal refraction correction when detecting an "inversion" of the refraction correction which, among said first and second refraction corrections, best corrects the subject's vision. Such an inversion may occur in the course of a sequence of successive executions of the set of steps S21 to S24, during which the average refractive correction is monotonously increased (or monotonously decreased). This inversion corresponds to the fact that the subject 5 signals, during a new execution of step S24, that it is not anymore the second refraction correction that best corrects his vision but that it is now the first refraction correction, or vice-versa. Such an inversion occurs when the average refractive correction mentioned above passes from one side to another side of the optimal refraction correction, in the coordinate system. Such an inversion thus reveals that the first and second correction refractions are close to the optimal refraction correction.

The control unit 3 may also determine that the first and second refraction corrections are close to the optimal refraction correction, on the basis of the former refraction prescription, or on the basis of the preliminary refraction prescription concerning the subject 5, acquired at step So.

Regarding now the gap between the first and second refraction corrections to be compared with each other, the control unit 3 may be programmed to determine the distance d12 between the first and second points P1, P2, at step S21, as a function of the sensitivity parameter of the subject, as explained at the beginning of the section "switching from the first to the second refraction correction".

The control unit 3 may also be programmed to determine the distance d12, in step S21, so that its value is smaller when the control unit 3 has determined that the first and second refraction corrections are close or are getting closer to the optimal refraction correction than when the first and second refraction corrections are considered far from the optimal refraction correction. For instance, the distance d12 may be set to an initial value of 1 diopter, and then be set to 0.5 diopter once the control unit 3 has determined that the first and second refraction corrections are close or are getting closer to the optimal refraction correction.

Regarding now step S22, in the embodiments described here, the control unit 3 is programmed so that:

if the control unit 3 had previously determined that the first and second refraction corrections were close to or were getting closer to the optimal refraction correction, for instance according to one of the criteria described above, then, the control unit concludes that an intermediate point of the medial part of the line segment [P1P2] is closer to the optimal refraction point $P_0$ than each of said first and second points P1, P2.

And when the control unit 3 has determined that this intermediate point of the medial part of the line segment [P1P2] is closer to the optimal refraction point $P_0$ than each of said first and second points P1, P2, the control unit 3 then determines the features of the switching from the first to this second refraction corrections according to the feature i), or to the feature ii) described above, that is to say so that the trajectory representing said switching avoids the intermediate point $P_I$, or passes in its vicinity at high speed.

And as long as the control unit 3 has not determined that an intermediate point of the medial part of the line segment [P1P2] is closer to the optimal refraction point $P_0$ than each of said first and second points P1, P2, the control unit 3 determines the features of said switching with no particular constraint, the trajectory representing the switching being for instance rectilinear and carried on at any, not necessary high, speed.

Alternatively, the control unit 3 may be programmed to determine whether an intermediate point of the medial part of the line segment [P1P2] is closer to, or alternatively farther from, the optimal refraction point $P_0$ than each of said first and second points P1, P2 on the basis of the coordinates of the first point P1, of the second point P2, and of an estimate of the optimal refraction point, $P_{OE}$. Such an estimate $P_{OE}$ of the optimal refraction point represents for instance a refractive power state corresponding to a former or preliminary refraction prescription of the subject 5. On the base of this estimate, the control unit 3 may then compute the values of:

the distance $d_{PI}$ between the intermediate point $P_I$ and the estimate of the optimal refraction point $P_{OE}$;

the distance $d_{P1}$ between the first point P1 and the estimate of the optimal refraction point $P_{OE}$; and the distance $d_{P2}$ between the second point P2 and the estimate of the optimal refraction point $P_{OE}$.

If the distance $d_{PI}$ is smaller (alternatively higher) than $d_{P1}$ and than $d_{P2}$, then the control unit 3 determines that the intermediate point considered is closer to (or alternatively farther from) the optimal refraction point $P_O$ than each of said first and second points P1, P2.

In the exemplary protocol described above, the control unit is programmed to test whether an intermediate point of the medial part of the line segment [P1P2] is closer to, or alternatively farther from, the optimal refraction point $P_O$ than each of said first and second points P1, P2, before controlling the optical system 2 so that the criteria of feature i) or ii) is fulfilled, during the switching.

However, in other embodiments, the control unit 3 may be programmed to determine the features of the switching from the first to the second refraction corrections in accordance with the feature i), or with the feature ii) described above systematically, regardless of any condition, that is to say all the time.

In this case, each time the optical system 2 switches from the first to the second refraction correction (and so, inter alia, in situations for which an intermediate point located on the medial part of the line segment is closer to, or farther from the optimal refraction point $P_O$ than each of the first and second points P1 and P2), the conditions corresponding to feature i) or to feature ii) are fulfilled. So, in these last embodiments, each time step S23 is executed, the conditions corresponding to feature i) or to feature ii) are fulfilled, regardless of any condition.

Besides, some operations carried on at step S21 or S22, like the determination of the speed of variation limit $s_L$, or the determination of the distance d12, may be executed just once, not each time these steps are executed.

The invention claimed is:

1. A method for providing at least one eye of a subject with a first refraction correction and with a second refraction correction to be compared with each other, in which an optical system transmits a light beam coming from a target object to the eye of the subject, the method comprising a step of switching the optical system from:

a first refractive power state, in which the optical system provides said first refraction correction to the eye of the subject, to a second refractive power state, in which the optical system provides said second refraction correction to the eye of the subject, said switching being carried on without interrupting the light beam transmitted by the optical system, each refractive power state of the optical system being represented by a corresponding point, in a coordinate system, the coordinates of said point being representatives of the values, for said refractive power state of the optical system, of different refractive power features of the optical system, for any refractive power state of the optical system, the coordinates of the point representing said refractive power state in the coordinate system comprising:

at least two of the followings: a spherical power, a first cylindrical power feature, and a second cylindrical feature of the optical system in said refractive power state, or at least two of the second order coefficients of a Zernike polynomials decomposition of a wave front outputted by the optical system in said refractive power state, the first refractive power state being represented by a first point and the second refractive power state being represented by a second point in said coordinate system, a line segment starting at said first point and ending at said second point, an optimal refraction correction for the eye of the subject being represented by an optimal refraction point in said coordinate system, said optimal refraction correction being the refraction correction that compensates for the refractive errors of the eye of the subject, wherein, when an intermediate point, located on a medial part of said line segment is closer to the optimal refraction point or farther from the optimal refraction point than each of said first and second points, then, said switching is carried on so that:

for each point of a trajectory representing said switching, a distance in said coordinate system between said point and the intermediate point is higher than or equal to one fourth of the smallest of: a first distance between said first point and said intermediate point, and a second distance between said second point and said intermediate point, or so that a speed of variation of a refractive power of said optical system, at the point of said trajectory that is the closest to said intermediate point, is higher than a speed of variation limit above which the subject is unable to perceive a refractive power variation, said speed of variation limit being the highest speed of variation of refractive power for which the subject is able to perceive a refractive power variation.

2. The method according to claim 1, wherein said switching is carried on so that:

an integral over time, from a beginning until an end of said switching, along the trajectory representing said switching, of a given function the argument of which being the distance between a current, variable point of said trajectory and said intermediate point, is smaller than an in-proximity time span limit multiplied by the value of said function when its argument is equal to one fourth of the smallest of said first distance and said second distance.

3. The method according to claim 2, wherein said in-proximity time span limit is comprised between 1 millisecond and 1 second.

4. The method according to claim 1, wherein said switching is carried on so that, for each point of the trajectory that represents said switching in said coordinate system, a distance between said point and said intermediate point is higher than or equal to the smallest of said first distance and said second distance.

5. The method according to claim 1, wherein, the intermediate point being the middle of said line segment, the trajectory that represents said switching in said coordinate system is a half circle centered on the intermediate point.

6. The method according to claim 1, wherein a spherical power of the optical system is varied during said switching, while remaining, all along said switching, higher than the smallest of: a first spherical power the optical system has in its first refractive power state, and a second spherical power the optical system has in its second refractive power state.

7. The method according to claim 1, comprising the following steps, executed before switching from said first refractive power state to said second refractive power state:
   acquiring data relative to a response speed with which said subject reacts to a refractive power change; and
   determining said speed of variation limit on the basis of said data.

8. The method according to claim 1, wherein said speed of variation limit is higher than or equal to 20 diopters per second.

9. The method according to claim 1, wherein the trajectory that represents said switching in said coordinate system is said line segment, and wherein the speed of variation of the refractive power of the optical system is higher than said speed of variation limit at the time when the point representing the refractive power state of the optical system passes through said intermediate point.

10. The method according to claim 1, wherein the optical system in its second refractive power state has the same spherical power as in its first refractive power state, and wherein at least one cylindrical power feature of the optical system is different in its second refractive power state than in its first refractive power state.

11. The method according to claim 1, wherein the medial part of said line segment has a length equal to one half of the length of said line segment, and wherein the middle of said medial part coincides with the middle of said line segment.

12. The method according to claim 1, wherein, all along said switching, for each point of said trajectory,
   a blur level, that is determined on the basis of a theoretical model of the eye and vision of the subject, and that takes into account that the eye of the subject is provided with a refraction correction corresponding to the refractive power state associated to said point, is:
      higher than the product of a margin coefficient by the minimum of a first blur level associated to the first refractive power state of the optical system and of a second blur level associated to the second refractive power state of the optical system, and
      smaller than the ratio of the maximum of the first blur level and the second blur level by the margin coefficient k,
   said first and second blur levels being determined on the basis of said theoretical model of the eye and vision of the subject and taking into account that said eye is provided with the first refraction correction, and with the second refraction correction respectively,
   said margin coefficient being comprised between 0.5 and 1.

13. The method according to claim 1, wherein said intermediate point is the middle of said line segment.

14. An instrument for providing at least one eye of a subject with a first refraction correction and with a second refraction correction to be compared with each other, comprising:
   an optical system set up to transmit, to the eye of the subject, a light beam coming from a target object; and
   a control unit for controlling said optical system, the control unit being programmed for switching the optical system from:
      a first refractive power state, in which the optical system provides said first refraction correction to the eye of the subject, to
      a second refractive power state, in which the optical system, provides said second refraction correction to the eye of the subject,
   the optical system being configured so that, during said switching, the light beam transmitted by the optical system is not interrupted,
   each refractive power state of the optical system being represented by a corresponding point, in a coordinate system, the coordinates of said point being representatives of the values, for said refractive power state of the optical system, of different refractive power features of the optical system, for any refractive power state of the optical system, the coordinates of the point representing said refractive power state in the coordinate system comprising:
      at least two of the followings: a spherical power, a first cylindrical power feature, and a second cylindrical feature of the optical system in said refractive power state, or
      at least two of the second order coefficients of a Zernike polynomials decomposition of a wave front outputted by the optical system in said refractive power state,
   the first refractive power state being represented by a first point and the second refractive power state being represented by a second point in said coordinate system, a line segment starting at said first point and ending at said second point, an optimal refraction correction for the eye of the subject being represented by an optimal refraction point in said coordinate system, said optimal refraction correction being the refraction correction that compensates for the refractive errors of the eye of the subject,
   wherein the control unit is programmed in order to control the optical system so that
   when an intermediate point, located on a medial part of said line segment is closer to the optimal refraction point or farther from the optimal refraction point than each of said first and second points,
   then, during said switching:
      for each point of a trajectory representing said switching in said coordinate system, a distance in said coordinate system between said point and the intermediate point is higher than or equal to one fourth of the smallest of: a first distance between said first point and said intermediate point, and a second distance between said a second point and said intermediate point; or
      a speed of variation of the refractive power of said optical system, at the point of said trajectory that is the closest to said intermediate point, is higher than a speed of variation limit above which the subject is unable to perceive a refractive power variation, said speed of variation limit being the highest speed of variation of refractive power for which the subject is able to perceive a refractive power variation.

* * * * *